United States Patent
West et al.

[11] Patent Number: 5,877,097
[45] Date of Patent: *Mar. 2, 1999

[54] DENSIFIED CELLULOSE FIBER PADS AND METHOD OF MAKING THE SAME

[75] Inventors: Hugh West, Tukwila; Colin Elston, Gig Harbor; Fred B. Howard, Olalla, all of Wash.

[73] Assignee: Weyerhaeuser Company

[ * ] Notice: This patent issued on a continued prosecution application filed under 37 CFR 1.53(d), and is subject to the twenty year patent term provisions of 35 U.S.C. 154(a)(2).

[21] Appl. No.: 552,593

[22] Filed: Nov. 3, 1995

Related U.S. Application Data

[63] Continuation of Ser. No. 337,642, Nov. 10, 1994, abandoned.

[51] Int. Cl.$^6$ ...................................................... B32B 7/02
[52] U.S. Cl. ..................... 442/327; 442/381; 442/393; 442/417; 264/257; 28/100
[58] Field of Search .................................. 428/288, 283, 428/218; 442/327, 381, 393, 417; 264/241, 257; 28/100

[56] References Cited

U.S. PATENT DOCUMENTS

| | | | |
|---|---|---|---|
| 4,458,042 | 7/1984 | Espy | 524/14 |
| 4,590,114 | 5/1986 | Holtman | 428/171 |
| 4,655,877 | 4/1987 | Horimoto et al. | 162/146 |
| 4,886,697 | 12/1989 | Perdelwitz, Jr. et al. | 428/192 |
| 4,980,226 | 12/1990 | Hellgren et al. . | |
| 5,064,689 | 11/1991 | Young, Sr. et al. | 427/202 |
| 5,217,445 | 6/1993 | Young et al. | 604/381 |
| 5,230,959 | 7/1993 | Young, Sr. et al. | 428/372 |
| 5,252,275 | 10/1993 | Sultze et al. | 264/119 |
| 5,547,745 | 8/1996 | Hansen et al. | 428/283 |
| 5,589,256 | 12/1996 | Hansen et al. | 428/283 |

FOREIGN PATENT DOCUMENTS

| | | |
|---|---|---|
| 0 070 164 | 1/1983 | European Pat. Off. . |
| 0 210 968 | 2/1987 | European Pat. Off. . |
| 0 340 763 A1 | 11/1989 | European Pat. Off. ........................ 8/6 |
| 1059617 | 3/1954 | France . |
| 1524804 | 10/1968 | France . |
| 2 234 008 | 1/1974 | Germany . |
| WO91/01396 | 2/1991 | WIPO . |
| WO 91/11162 | 8/1991 | WIPO ....................................... 13/15 |
| WO 91/11165 | 8/1991 | WIPO ....................................... 13/52 |

OTHER PUBLICATIONS

*PULPEX® Polyolefin Pulps* Product Brochure, Hercule Incorporated, (No Date).
Wilson, H.D., "Characterization of PULPEX® E–338 Thermall Bonded Absorbent Cores," Section IV, Absorbent Product Conference (Sep. 23–24, 1987), pp. 1–41.
Bither, P.G., "Thermally Bonded Cores Add Value to Absorben Products," *Nonwovens World*, pp. 63–68 (Jan. 1988).
*Absorbent Matters*, vol. 2, No. 1, pp. 1–4 (Mar. 1988).
*Absorbent Matters*, vol. 2, No. 2, pp. 1–4 (Sep. 1988).
Hanson, J.P., "Roses Have Thorns: Performance Issues fo Thermal–Bonding Fibers," *Nonwovens World*, pp. 71–73 (Sep. 1988).

(List continued on next page.)

*Primary Examiner*—Christopher Raimund
*Attorney, Agent, or Firm*—Christensen O'Connor Johnson & Kindness PLLC

[57] ABSTRACT

A densified web of cellulose fibers has a high absorbent capacity and good wet strength. The web is produced by combining cellulose fibers with a bonding agent, activating the bonding agent, allowing it to contact the cellulose fibers, and thereafter deactivating the bonding agent. The web is thereafter compressed in a cooled state to form a densified web. The web exhibits an absorbent capacity superior to that of prior densified and bonded webs.

63 Claims, 1 Drawing Sheet

OTHER PUBLICATIONS

Apostolico, S.C., "Thermal Bonding of Absorbent Cores," Sectio VIII, Nonwovens Management/Specialty Markets Conferenc (Mar. 20–21, 1989), pp. 1–13.

*Textile Fibers/Hoechst Celanese Corporation/Celbond® Stapl Fibers*Product Brochure, Hoechst Celanese Corporation, Mar. 1991.

Wilson, H.D., and Engle, E.J., "Fluid Transport in Thermally Bonde Cellulose Pads," In *Nonwovens: An Advanced Tutorial*, eds. A.F. Turbak and T.L. Vigo, pp. 241–270, (No Date).

Lanigan, W.R., "The Hercules Absorbent Products Laboratory: A Tool for the Industry," Section IV, pp. 1–12, (No Date).

*Fig.2.*

DENSIFIED CELLULOSE FIBER PADS AND METHOD OF MAKING THE SAME

RELATED APPLICATIONS

The present application is a continuation of previous copending application Ser. No. 08/337,642, filed Nov. 10, 1994, now abandoned. The benefit of the filing date of the previous application is claimed under 35 U.S.C. § 120.

FIELD OF THE INVENTION

The present invention relates to cellulose fiber pads, more particularly to cellulose fiber pads in which the fibers have been bonded together and the pads densified, and more particularly to such pads having an increased absorbent capacity and good wet pad integrity relative to prior pads.

BACKGROUND OF THE INVENTION

Cellulose fibers derived from wood pulp are used in a variety of absorbent articles, for example, diapers and feminine hygiene products. It is desirable for the absorbent articles to have a high absorbent capacity for liquid, as well as to have good strength characteristics for durability. Cellulose fibers for pad formation have traditionally been shipped to end users, that is, manufacturers of absorbent articles, in large densified rolls, or less frequently in compressed bale form. The end user fluffs the cellulose fibers, combines them with additives, such as absorbency enhancing polymers or specially engineered fibers, forms them into a pad, and then forms them into an absorbent article for the consumer. While this methodology is effective, it is desirable for some applications to provide absorbent webs that include additives to the manufacturer of the absorbent article in a form that can be incorporated directly into the absorbent article without the intermediate steps of fluffing, additive incorporation, and pad construction.

It is desirable to density webs before forming them into a roll to decrease the shipping costs. However, densified webs have insufficient strength for incorporation directly into absorbent structures. Therefore, the strength of the web must be increased, for example, by bonding the fibers together. The prior art suggests the simultaneous heating and compressing of a cellulose fiber web that has been combined with a thermoplastic bonding material to form a densified web with increased integrity. While this densifying technique provides higher bulk density and strength compared to densified webs of conventional non-bonded pulp, it has been found that the resulting densified web has a lower capacity for absorbing liquid than the non-densified, or fluffed, material normally incorporated into absorbent structures.

It is therefore desirable to provide a densified web of cellulose fibers that has an absorbent capacity superior to prior densified webs, and that has a wet integrity or strength that is substantially higher than non-bonded, densified webs.

SUMMARY OF THE INVENTION

In accordance with the teaching in the following specification, the present invention provides a fibrous article comprising a densified web of cellulose fibers and a bonding agent. At least some of the fibers of the web are bound together by activating the bonding agent prior to densification. The web is densified after the bonding agent has been deactivated and has bound the fibers together. In a most preferred form, the densified web has a minimum density of at least equal to or greater than 0.1 grams per cc. The resulting densified web has an absorbent capacity for synthetic urine that is significantly greater than the absorbent capacity for synthetic urine exhibited by a comparable web of cellulose fibers bound together by a bonding agent, which the comparable web has been densified to substantially the same degree as the densified web of the present invention by activating the bonding agent and densifying the web while the bonding agent is active.

The densified web of the present invention can be formed into absorbent articles comprising one or more layers. For example, the present invention can take the form of a single absorbent layer composed of a densified web produced in accordance with the present invention. The densified web of the present invention can also be incorporated into multi-layer articles including, for example, an upper acquisition/distribution layer and a storage layer. In accordance with the teachings herein, the densified web produced with the present invention can be included in one or both of the acquisition/distribution layer and a lower storage layer.

A densified web is produced in accordance with the present invention by first forming, for example, a web of cellulose fibers containing a bonding agent, thereafter activating the bonding agent so that the bonding agent contacts at least some of the cellulose fibers, deactivating the bonding agent to bind at least some of the cellulose fibers together, and thereafter densifying the bonded web of cellulose fibers to a density of at least about 0.1 grams per cc.

BRIEF DESCRIPTION OF THE DRAWINGS

A better understanding of the present invention can be derived by reading the ensuing specification in conjunction with the accompanying drawings, wherein.

DETAILED DESCRIPTION OF THE PREFERRED EMBODIMENT

Cellulosic fibers are the basic component of the densified webs produced in accordance with the present invention. Although available from other sources, cellulosic fibers are currently derived primarily from wood pulp. Suitable wood pulp fibers for use with the invention can be obtained from well-known chemical processes such as the Kraft and sulfite processes, whether bleached or unbleached. The pulp fibers may also be processed by thermomechanical, chemithermomechanical methods, or combinations thereof. The preferred pulp fiber is chemical. The preferred starting material is prepared from long fiber coniferous wood species, such as southern pine, Douglas fir, spruce, and hemlock. Ground wood fibers, recycled or secondary wood pulp fibers, and bleached and unbleached wood pulp fibers can be used. Details of the production of wood pulp fibers are well-known to those skilled in the art. These fibers are commercially available from a number of companies, including Weyerhaeuser Company, the assignee of the present invention. For example, suitable cellulose fibers produced from southern pine that are usable with the present invention are available from Weyerhaeuser Company under the designations NB316 and NB416.

The wood pulp fibers of the present invention can also be pretreated prior to use with the present invention. This pretreatment may include physical treatment, such as subjecting the fibers to steam, or chemical treatment, for example, cross-linking the cellulose fibers using any of a variety of conventional cross-linking agents such as dimethyldihydroxyethyleneurea. Cross-linking the fibers, for example, increases their resiliency, and thereby can improve their absorbency. The fibers may also be twisted or crimped, as desired. Suitable cross-linked cellulose fibers produced from southern pine are available from Weyerhaeuser Company under the designation HB416.

Cellulosic fibers treated with particle binders and/or densification/softness aids known in the art can also be employed in accordance with the present invention. The particle binders serve to attach other materials, such as superabsorbent polymers, to the cellulosic fibers. Cellulosic fibers treated with suitable particle binders and/or densification/softness aids and the process for combining them with cellulose fibers are disclosed in the following U.S. patents and patent applications: (1) U.S. Pat. No. 5,543,215, entitled "Polymeric Binders for Binding Particles to Fibers;" (2) U.S. Pat. No. 5,538,785 entitled "Non-Polymeric Organic Binders for Binding Particles to Fibers;" (3) U.S. Pat. No. 5,300,192, entitled "Wet Laid Fiber Sheet Manufacturing With Reactivatable Binders for Binding Particles to Binders;" (4) U.S. Pat. No. 5,352,480, entitled "Reactivatable Binders for Binding Particle to Fibers;" (5) U.S. Pat. No. 5,308,896, entitled "Particle Binders for High-Bulk Fibers;" (6) U.S. Pat. No. 5,589,256 entitled "Particle Binders that Enhance Fiber Densification;" (7) U.S. Pat. No. 5,672,418, entitled "Particle Binders;" (8) U.S. Pat. No. 5,607,759, entitled "Particle Binding to Fibers;" (9) U.S. Pat. No. 5,693,411, entitled "Binders for Binding Water Soluble Particles to, Fibers;" (10) U.S. Pat. No. 5,547,745, entitled "Particle Binders;" (11) U.S. Pat. No. 5,641,561, entitled "Particle Binding to Fibers;" and (12) U.S. Pat. No. 5,447,977, entitled "Particle Binders for High-Bulk Fibers," all expressly incorporated herein by reference. One example of a suitable densification/softness aid is a mixture of 70% sorbitol and 30% glycerin. The pulp is treated with sorbitol and glycerin by spraying the pulp sheet with the mixture and passing the sheet through a roll coater, or other means of adding a liquid to a pulp sheet familiar to those skilled in the art.

Although not to be construed as a limitation, examples of pretreating fibers include the application of fire retardants to the fibers, such as by spraying the fibers with fire-retardant chemicals. Specific fire-retardant chemicals include, by way of example, sodium boratelboric acid, urea, urea/phosphates, etc. In addition, the fibers may be pretreated with surfactants or other liquids, such as water or solvents, which modify the surface of the fibers. Other pretreatments include exposure to antimicrobials, pigments and densification or softening agents. Fibers pretreated with other chemicals, such as thermoplastic and thermosetting resins also may be used. Combinations of pretreatments also may be employed with the resulting pretreated fibers then being subjected to the application of the binder as explained below.

Bonding agents useful in accordance with the present invention are those materials that (a) are capable of being combined with and dispersed throughout a web of cellulosic fibers, (b) when activated, are capable of coating or otherwise adhering to the fibers or forming a binding matrix, and (c) when deactivated, are capable of binding at least some of the fibers together. It is important that the binding action of the agent occur while the fibers are at a low density, and that densification occurs only after the binding agent is deactivated.

Suitable bonding agents include thermoplastic materials that are activated by melting at temperatures above room temperature. When these materials are melted, they will coat at least portions of the cellulose fibers with which they are combined. When the thermoplastic bonding agents are deactivated by cooling to a temperature below their melt point, and preferably no lower than room temperature, the bonding agent will upon solidifying from the melted state cause the cellulose fibers to be bound in a matrix.

Thermoplastic materials are the preferred binders, and can be combined with the fibers in the form of particles, emulsions, or as fibers. Suitable fibers can include those made from thermoplastic polymers, cellulosic or other fibers coated with thermoplastic polymers, and multi-component fibers in which at least one of the components of the fiber comprises a thermoplastic polymer. Single and multicomponent fibers are manufactured from polyester, polyethylene, polypropylene and other conventional thermoplastic fiber materials. The same thermoplastics can be used in particulate or emulsion form. Many single component fibers are readily available on the open market. Suitable multicomponent fibers include Celbon® fibers available from Hoechst Celanese Company. Suitable coated fibers can include cellulose fibers coated with latex or other thermoplastics, as disclosed in U.S. Pat. No. 5,230,959, issued Jul. 27, 1993, to Young et al., and U.S. Pat. No. 5,064,689, issued Nov. 12, 1991, to Young et al. The thermoplastic fibers are preferably combined with the cellulose fibers before or during the laying process. When used in particulate or emulsion form, the thermoplastics can be combined with the cellulose fibers before, during, or after the laying process.

Other suitable thermoplastic bonding agents include ethylene vinyl alcohol, polyvinyl acetate, acrylics, polyvinyl acetate acrylate, polyvinyl dichloride, ethylene vinyl acetate, ethylene vinyl chloride, polyvinyl chloride, styrene, styrene acrylate, styrene butadiene, styrene acrylonitrile, butadiene acrylonitrile, acrylonitrile butadiene styrene, ethylene acrylic acid, urethanes, polycarbonate, polyphenylene oxide, and polyimides.

Thermosetting materials also serve as excellent bonding agents for the present invention. Typical thermosetting materials are activated by heating to elevated temperatures at which cross-linking occurs. Alternatively, a resin can be activated by combining it with a suitable cross-linking catalyst before or after it has been applied to the cellulosic fiber. Thermosetting resins can be deactivated by allowing the cross-linking process to run to completion or by cooling to room temperature, at which point cross-linking ceases. When cross-linked, it is believed that the thermosetting materials form a matrix to bond the cellulose fibers. It is contemplated that other types of bonding agents can also be employed, for example, those that are activated by contact with steam, moisture, microwave energy, and other conventional means of activation.

Thermosetting bonding agents suitable for the present invention include phenolic resins, polyvinyl acetates, urea formaldehyde, melamine formaldehyde, and acrylics. Other thermosetting bonding agents include epoxy, phenolic, bismaleimide, polyimide, melamine formaldehyde, polyester, urethanes, and urea.

These binders are normally combined with the fibers in the form of an aqueous emulsion. They can be combined with the fibers during the laying process. Alternatively, they can be sprayed onto a loose web after it has been formed.

Materials that enhance absorbent capacity, such as superabsorbent polymers, can also be combined with the densified web produced in accordance with the present invention. A superabsorbent polymer as used herein is a polymeric material that is capable of absorbing large quantities of fluid by swelling and forming a hydrated gel (hydrogel). The superabsorbent polymers also can retain significant amounts of water under moderate pressures. Superabsorbent polymers generally fall into three classes, namely, starch graft copolymers, cross-linked carboxymethylcellulose derivatives and modified hydrophilic polyacrylates. Examples of such absorbent polymers are hydrolyzed starch-acrylonitrile graft copolymer, a neutralized starch-acrylic acid graft copolymer, a saponified acrylic acid ester-vinyl acetate copolymer, a hydrolyzed acrylonitrile copolymer or acrylamide copolymer, a modified cross-linked polyvinyl alcohol, a neutralized self-cross-linking polyacrylic acid, a cross-linked polyacrylate salt, carboxylated cellulose, and a neutralized cross-linked isobutylene-maleic anhydride copolymer. The superabsorbent polymers can be combined with the cellulosic fibers in amounts up to 70% by weight based on the total weight of fibers and polymer. Superabsorbent polymers are available commercially, for example, starch graft polyacrylate hydrogel fines from Hoechst-Celanese of Portsmouth, Va. These superabsorbent polymers come in a variety of sizes, morphologies and absorbent properties. These are available from Hoechst-Celanese under trade designations such as IM 1000 and IM 3500. Other superabsorbent particles are marketed under the trademarks SAN-WET (supplied by Sanyo Kasei Kogyo Kabushiki Kaisha), SUMIKA GEL (supplied by Sumitomo Kagaku Kabushiki Kaisha), which is suspension polymerized and spherical, as opposed to solution polymerized ground particles, FAVOR (supplied by Stockhausen of Greensboro, N.C.), and NOR-SOCRYL (supplied by Atochem). Other superabsorbent polymers are described in U.S. Pat. No. 4,160,059; U.S. Pat. No. 4,676,784; U.S. Pat. No. 4,673,402; U.S. Pat. No. 5,002,814; U.S. Pat. No. 5,057,166; U.S. Pat. No. 4,102,340; and U.S. Pat. No. 4,818,598, expressly incorporated herein by reference. Products such as diapers that incorporate superabsorbent polymers are shown in U.S. Pat. No. 3,669,103 and U.S. Pat. No. 3,670,731.

Figure 1:
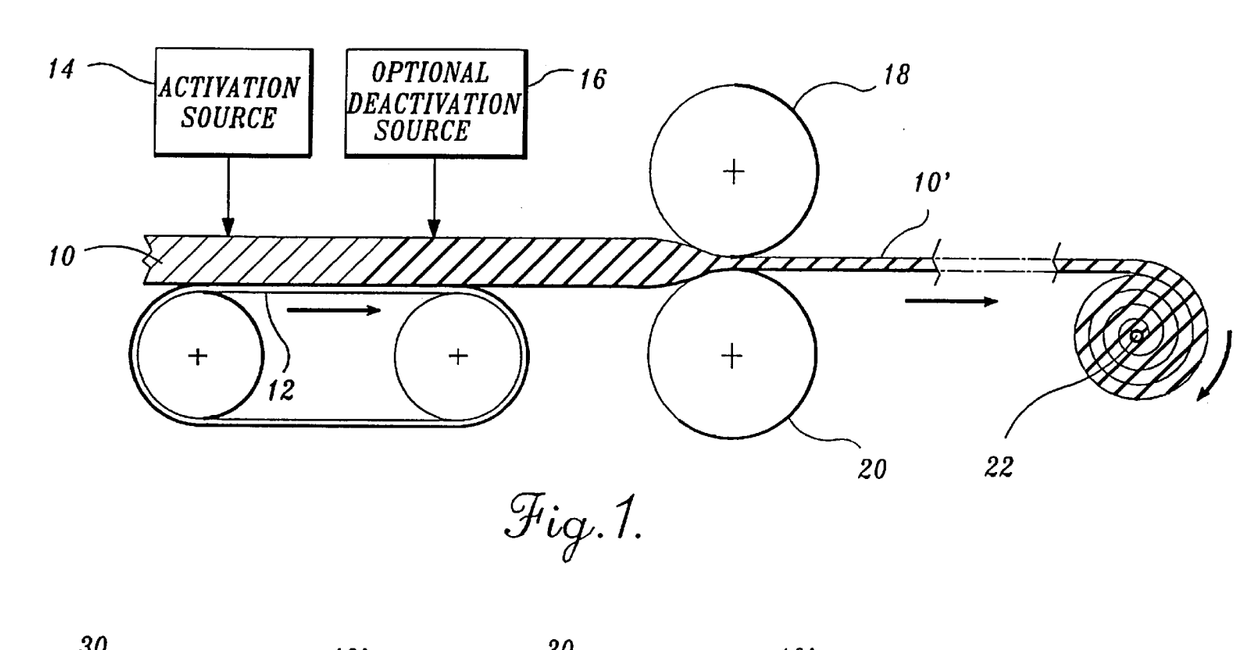
FIG. 1 is a schematic view showing a web of cellulose fibers containing a bonding agent that is first activated and then deactivated, with the web thereafter being densified.

Referring now to FIG. 1, one method for densifying cellulose fibers in accordance with the present invention is illustrated. A web 10 of cellulosic fibers can be laid on a conveyor 12 using conventional air-laying techniques. The web 10 of cellulose fibers may be combined with a bonding agent of the type described above before, after, or as it is being laid down. The bonding agent can be used in any concentration that will achieve the desired result, that is, binding at least some of the fibers together after the bonding agent has been deactivated. The bonding agents disclosed above can be incorporated with the cellulose fibers in an amount ranging up to, for example, 70%, based on the weight of the fiber and bonding agent.

The web 10 can then be forwarded past an activation station 12, in the preferred embodiment a heat source. Heat can be supplied from the heat source 12 by means of hot air, infrared radiation, or one of many other conventional heat sources available to one of ordinary skill. Heat can be applied to the web as it passes under the heat source to activate the bonding agent. In the case of the typical thermoplastic materials, for example, the heat source melts the bonding agent so that it will adhere to or form a bonding network for the cellulosic fibers. For the typical thermoplastic materials listed above, the heat source must heat the bonding agent to well above room temperature. For example, polyethylene must be heated to temperatures on the order of 140° to 145° C. These temperatures, of course, are well under that which will cause damage to the bonding agent and/or the cellulose fiber. The bonding agent is then deactivated to bind the cellulose fibers of the web together. In the case of the heat activated bonding agents specifically described above, deactivation occurs by cooling the bonding agents. Cooling can be allowed to occur naturally over time under room temperature conditions. Optionally, the web can be passed under a deactivation source 16, for example a cooling source. The cooling source, for example, can be a stream of room temperature or refrigerated air that is blown onto or through the web 10 to deactivate the bonding agent.

The web 10 is then passed between a pair of nip rolls 18 and 20, which compress or density the deactivated, bonded web to a density significantly greater than in its original air-laid condition. In accordance with the present invention, it is preferred that the densified web 10' be compressed to a density of at least 0.1 grams per cc, preferably from 0.1 to 0.7 grams per cc, and most preferably from 0.3 to 0.7 grams per cc. The densified web 10' can then be forwarded to a winding station, where the web is slit and wound onto a core 22 to form a roll of densified material suitable for handling and shipment. Upon arriving at the end user's facility, the densified web can be unrolled, cut and used in absorbent constructs.

The densified webs prepared in accordance with the present invention have a wet pad integrity that is greater than the wet pad integrity of a non-bonded, densified web of cellulose fibers that has been densified to substantially the same degree. This is a direct result of employing a bonding agent to cause at least a portion of the cellulose fibers to adhere to each other. While prior experiments with hot pressing resulted in lower absorbent capacity for densified webs, the absorbent capacity of the densified web produced in accordance with the present invention is at least about equivalent to the absorbent capacity of a non-bonded, densified web of cellulose fibers. It has also been found that the web densified in accordance with the present invention, that is, a web that is densified after the bonding agent has been deactivated so that the cellulose fibers are bound together, has an absorbent capacity that is significantly greater than prior bonded webs. Specifically, the web of the present invention has an absorbent capacity that is significantly greater than the absorbent capacity of a comparable web of cellulose fibers bound together by a bonding agent in which the web was densified to substantially the same degree as that in accordance with the present invention, but was densified while the bonding agent was still active.

Absorbent capacity as used herein is the capacity for a web of cellulose fibers to absorb aqueous solutions of metal and alkali salts of inorganic and organic acids. Examples of such solutions include natural body fluids, such as urine, blood, and menstrual fluids. For purposes of illustration, comparison, and definition, a standard solution of synthetic urine is chosen. The standard synthetic urine is defined specifically in the following examples.

Furthermore, the invention has been described in conjunction with first air-laying a loose web of cellulose fibers and thereafter densifying in accordance with the present invention. The densification method will also work with wet-laid fibers. Normally, fibers that are formed into webs using wet-laid processes are inherently relatively dense. Wet-laid fiber webs are also usable in the present invention by first fluffing or fiberizing the wet-laid web, and thereafter forming a loose web and densifying it in accordance with the present invention.

Figure 2:
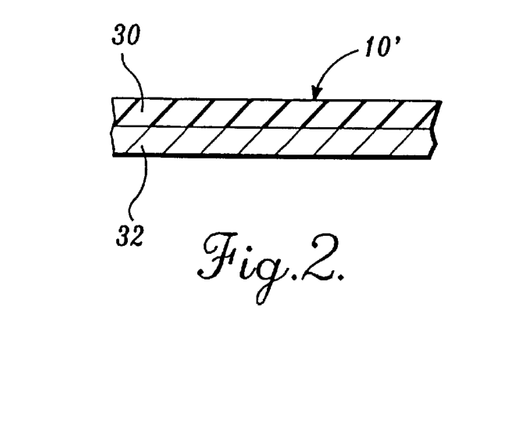
FIGS. 2, 3 and 4 are schematic cross-sectional views of various absorbent structures constructed using the densified web produced in accordance with the present invention.
Figure 3:
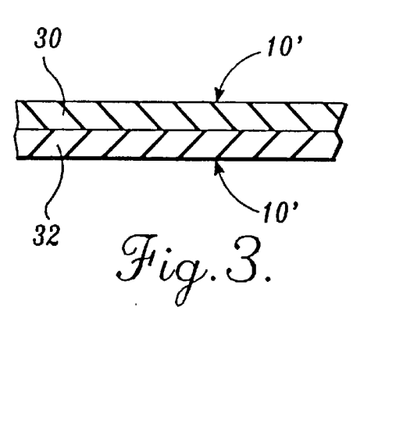
Figure 4:
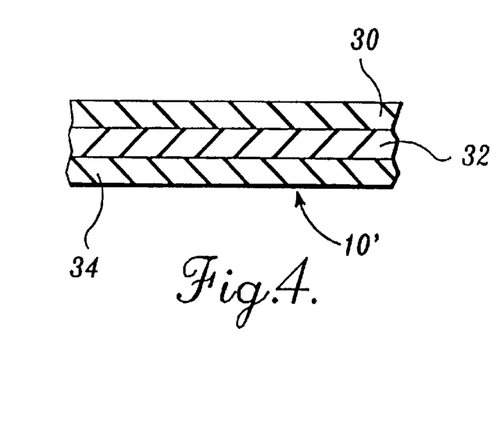

The densified bonded web 10' produced in accordance with the process described above and depicted in FIG. 1 can be incorporated in an absorbent article as the absorbent layer. It can be used alone, or as illustrated in FIG. 2, can be used in combination with secondary layers. In FIG. 2, the web 10' is employed as an upper acquisition/distribution layer in combination with a storage layer 32. Storage layer 32, if desired, can also comprise a densified layer of bonded cellulose fibers 10', as illustrated in FIG. 3. And finally, as illustrated in FIG. 4, a third base layer 34 can also be employed if desired, with a storage layer 32 and an acquisition layer 30. If desired, the retention layer 34 can also be composed of the densified bonded web 10' constructed in accordance with the present invention.

EXAMPLES

Experimental Procedures:

All absorbent pads were formed in the laboratory on a 6" diameter circular laboratory pad former. The pad former was equipped with a pin mill fluffing device. The pad former replicates in the laboratory air-laid webs produced with full-scale commercial equipment. Additives, including bonding agent and superabsorbent polymer, were added and combined with the cellulose fibers in the pad former. Homogenous blending of the pad components was achieved by refeeding the pad through the pin mill at least three times.

The 6" diameter pads were subjected to one of three bonding and/or densification procedures. The first densification procedure is referred to as "Cold Pressing." Cold Pressing is accomplished by placing the pad in a laboratory platen press and compressing it at ambient temperatures. The second densification procedure is referred to as "Hot Pressing." Hot Pressing is achieved by placing the pad in a laboratory platen press at a temperature elevated above ambient (platen temperature on the order of 170° C.). The third densification procedure, performed in accordance with the teachings of the present invention, is referred to in the Examples as "Thermobonding/cold pressing." Thermobonding/cold pressing is achieved by passing hot air (on the order of 170° C.) through a pad at its initial as-formed density (typically on the order of 0.05 grams per cc), followed by cooling to room temperature at the low density and by subsequent Cold Pressing. In all three of the densification procedures, final pad density is controlled by varying the pressure applied by the platen press to the pad. Rectangular pads measuring 4"×4" (10 cm.×10 cm.) are cut from the 6" diameter pad using die cutters, and are tested for capacity and strength using the following procedures.

An Inclined Plane Capacity test is performed by initially recording the pad weight $W_1$ in grams. One edge of the pad is immersed in the test liquid while the pad is supported on a glass plate inclined at 10° to the horizontal. Liquid is allowed to wick to the top edge of the pad. The inclined plane is reversed so that the pad then lies at the top of the slope and the liquid is applied at a controlled rate (5 ml. per minute) to the upper edge of the pad. When liquid breaks away from the lower edge of the pad, the test is stopped and the pad reweighed as $W_2$ in grams. The Inclined Plane Capacity is reported as $(W_2-W_1)/W_1$ in grams per gram.

An Ultimate Capacity test is performed by recording the initial pad weight $W_1$ in grams. The pad is then placed on a wire support screen and immersed in the test liquid in a horizontal position for 30 minutes. The pad is removed from the screen and allowed to drain in a horizontal position for five minutes. The pad is reweighed as $W_2(g)$. Ultimate capacity is reported as $(W_2-W_1)/W_1$ in grams per gram. (When the pad contains a coated fiber as described below, the weight $W_1$ in the denominator is adjusted by subtracting from its weight the coating polymer contained in the coated fiber.)

A Wet Pad Integrity test is performed by clamping a wet pad along two opposing sides, leaving about 3" of pad length visible, and suspending it vertically. A light plastic jug is suspended from the lower side of the sample. Water is run into the jug at a controlled rate of 200 ml per minute to apply a constantly increasing load to the sample. When the pad fails under the applied tension load, the water flow is stopped and the combined weight of the jug, water, lower clamp, and failed lower half of sample is recorded as X in grams. Wet integrity is reported as X in grams. (Note: If the pad fails under its own saturated weight after mounting vertically, the lower half of the failed sample is weighed and reported as the integrity X. If the pad is too weak to mount on the clamps, its integrity is reported as zero.)

The aqueous solution used in the tests is a synthetic urine available from National Scientific under the trade name RICCA. It is a saline solution containing 135 meq./l sodium, 8.6 meq./l calcium, 7.7 meq./l magnesium, 1.94% urea by weight (based on total weight), plus other ingredients.

The cellulose fibers used in the following examples are bleached southern pine Kraft fluff pulp available from the Weyerhaeuser Company. Fibers bleached with an elemental chlorine bleach are referred to by the trade designation NB316. Fibers bleached with a chlorine dioxide instead of chlorine are referred to by the designation NB416. A first bonding agent comprises a thermoplastic bicomponent fiber available from the Hoechst Celanese Co. under the trade name Celbond K56. Celbond K56 has a fiber length of 5 mm. The bicomponent fiber is comprised of a polyester core and a polyethylene sheath in a concentric extrusion. A cross-linked cellulose fiber was also employed. The cross-linked fiber comprised NB316 or NB416 cross-linked with dimethylol dihydroxyethylene urea. This cross-linked fiber is also available from the Weyerhaeuser Company, and will be referred to as the high-bulk additive (HBA) fiber. A coated fiber, hereinafter referred to as CCF, was also used as a bonding agent. The coated fiber was produced from NB316 or HBA coated with a polyvinyl acetate latex polymer available from the Reichold Company under designations "Latex 97-910" or "40-504". The latex polymer is coated on the fiber at a loading of 25% by weight based on the dry-coated fiber. Superabsorbent polymers are also incorporated into some of the pads. The superabsorbent polymer (SAP) used in these tests are available from the Hoechst Celanese Co. under the designations IM1000 and IM3500.

Example 1

This example illustrates that bonding of pads by Hot Pressing in the presence of bonding agents at densities at or above 0.1 grams per cc results in a catastrophic loss of capacity relative to a non-bonded pad. The example also illustrates that the loss of capacity is exacerbated at high densities, and that the capacity loss at high density cannot be restored by the addition of SAP.

Pads having a basis weight of 550 g/m² were formed from combinations of either HBA, CCF made from HBA (with 97-910 latex) or an 80/20 weight blend of HBA and Celbond K56 combined with SAP at levels of 15% and 45% total pad weight. All fiber SAP combinations were made at three density levels (minimum, 0.1 gram per cc; medium, 0.3 grams per cc; and high, 0.5 grams per cc). HBA pads containing no binder or other additives served as controls.

The 0.1 g/cc HBA pads were Cold Pressed (for 30 seconds) and the 0.3 and 0.5 g/cc HBA pads were Hot Pressed at 100° C. for 30 seconds. Hot Pressing was found necessary to achieve stable pad density because rapid springback in the Cold Pressed HBA pads resulted in equilibrium densities on the order of 0.15 g/cc or less. It should be noted, however, that no interfiber bonding took place in the Hot Pressed HBA control pads.

CCF and HBA/bicomponent fiber pads were all hot pressed at 140° C. for 30 seconds to form interfiber bond. Pads were then tested for Inclined Plane Capacity. The tests were each repeated three times, and the results averaged.

The averaged results are shown in Table 1.

TABLE 1

| SAP Level (%) | Density (g/cc) | HBA Control (no binder) | CCF from HBA | HBA with Celbond |
|---|---|---|---|---|
| | | Inclined Plane Capacity (g/g) | | |
| 15 | 0.1 | 17.3 | 12.9 | 10.8 |
| 15 | 0.3 | 13.3 | 5.1 | 4.5 |
| 15 | 0.5 | 11.8 | 2.5 | 3.4 |
| 45 | 0.1 | 22.5 | 19.6 | 11.2 |
| 45 | 0.3 | 20.6 | 9.5 | 8.1 |
| 45 | 0.5 | 15.7 | 3.8 | 7.4 |

Example 2

This example illustrates that bonding the fibers in the pad first at the lowest possible density, followed by cooling and subsequent pressing (Thermobonding/cold pressing), maintains the capacity of an equivalent non-bonded pad. This example also illustrates that considerable wet pad integrity can be imparted without loss of capacity by this Thermobonding/cold pressing process.

Pads having a basis weight of 550 g/m² were formed from combinations of NB316 CCF made from NB316 (with 40-504 latex coating), and a 95/5 weight blend of NB316 and Celbond K56, all containing IM1000 SAP at levels of 15% or 30%, based on total pad weight. All pads were produced at a density of 0.3 g/cc. The NB316 controls were Cold Pressed. The pads containing a bonding agent were prepared either by Hot Pressing at 170° C. for one minute, or by Thermobonding/cold pressing, by first heating the pad to 170° C. for one minute, followed by 2-hour cooling, followed by pressing to the desired density. All pads were tested for Ultimate Capacity and Wet Pad Integrity. Each test was repeated and the results averaged. The results shown in Table 2 below are the average of two samples.

TABLE 2

| Pad Type | Hot Pressed | | Thermobonded and Cold Pressed | | Relevant SAP Level Control NB3 16 | |
|---|---|---|---|---|---|---|
| | Ultimate Capacity g/g | Wet Pad Integrity (g) | Ultimate Capacity g/g | Wet Pad Integrity (g) | Ultimate Capacity g/g | Wet Pad Integrity (g) |
| | | | | | 15% SAP | |
| CCF from NB316 w/15% SAP | 11.3 | 2092 | 32.4 | 135 | 30.4 | 67 |
| | | | | | 30% SAP | |
| CCF from NB316 w/30% SAP | 16.9 | 1317 | 38.6 | 125.6 | 36.7 | 0 |
| | | | | | 15% SAP | |
| NB316 w/5% Celbond w/15% SAP | —* | —* | 30.4 | 325 | 30.4 | 67 |
| | | | | | 30% SAP | |
| NB316 w/5% Celbond w/30% SAP | —* | —* | 35.5 | 133 | 36.7 | 0 |

*Not measured.

Example 3

This example illustrates the use of HBA fiber to provide additional absorbent capacity in a Thermobonded/cold pressed pad. These results are shown without the enhancing capability of the SAP.

Pads having a basis weight of 550 grams per square meter were formed from NB 416, and formaldehyde free HBA made from NB 416 cross-linked with dimethyldihydroxyethyleneurea. The cellulosic fibers were combined with 5% by weight of a binding agent (Celbond 105). The pads were Thermobonded/cold pressed to a density of 0.3 g/cc. Each test was repeated and the results averaged. The pads were tested for ultimate capacity and wet pad integrity as described above. The results are set forth in Table 3 below.

TABLE 3

| Pad Type | Ultimate Capacity (g/g) | Wet Pad Integrity (g) |
|---|---|---|
| NB416 | 13.3 | 1959 |
| HBA(NB416) | 17.4 | 1685 |

Example 4

This example is intended to show that the present invention is useful with cellulosic fibers that have been combined with particle binders of the type described in the specification. NB416 cellulose fibers, commercially available from Weyerhaeuser Company, were prepared with densification/softness aids by spraying a fiber web with an aqueous solution of 70% by weight sorbitol and 30% by weight glycerin at a level of 9% by weight based on oven dried fiber, sorbitol and glycerin. These fibers were admixed with 10% by weight thermoplastic fiber, Celbond K56, based on the total fiber and densification/softness aids. Densified webs containing 0, 15%, and 45% by weight based on total weight of superabsorbent polymer (SAP) were prepared from the densification/softness aids coated cellulose fiber. The SAP used in this example was IM3500 from Hoechst-Celanese. One set of webs was Hot Pressed while a second set of webs was Thermobonded/cold pressed (by heating to approximately 170° C. followed by 2 hours of cooling at room temperature followed by pressing). Pads were prepared for the webs as in the previous examples. Each pad was tested for absorbent capacity using the inclined plane test. Each test was replicated three times and the results averaged. The results showing a significant increase in absorbent capacity using the techniques of the present invention are tabulated in the following Table 4 below.

TABLE 4

| % SAP | Hot Pressed Inclined Plane Capacity (g/g) | Thermobonded/ Cold Pressed Inclined Plane Capacity (g/g) |
| --- | --- | --- |
| 6 | 4.6 | 8.9 |
| 15 | 6.4 | 13.6 |
| 45 | 7.8 | 15.0 |

The foregoing examples are intended to be representative and to assist one of ordinary skill in the art in reproducing the invention as disclosed herein. They are not intended in any way to delimit the invention. The present invention has therefore been described in conjunction with preferred embodiments thereof One of ordinary skill will understand that various changes, substitutions of equivalents, and other alterations can be made to the invention without departing from the broad concepts disclosed herein. For example, the absorbent capacity of the cellulose web constructed in accordance with the present invention has only for comparative purposes been defined in the context of its ability to absorb synthetic urine. It is, however, intended that the claims be interpreted broadly to encompass cellulose webs capable of absorbing a variety of aqueous fluids. It is also intended that the present invention be limited in its scope only by the definition contained in the appended claims and equivalents thereof The embodiments of the invention in which an exclusive property or privilege is claimed are defined as follows:

1. A fibrous article comprising:
    a densified web of cellulose fibers, at least some of said fibers being bonded together by an activatable bonding agent comprising a water insoluble thermoplastic or thermosetting material, said densified web having a minimum density at least equal to or greater than 0.1 g/cc, based on the weight of the fiber and bonding material, said web having been densified after the bonding agent has been deactivated and has bound the fibers together, said web having been densified while the bonding agent is deactivated, the densified web having an absorbent capacity for synthetic urine that is greater than the absorbent capacity for synthetic urine exhibited by a comparable web of cellulose fibers bound together by a bonding agent in which the comparable web has been densified to substantially the same degree as said densified web by activating the bonding agent and densifying the comparable web while the bonding agent is active.

2. The article of claim 1, wherein the density of the web ranges from 0.1 g/cc to 0.7 g/cc.

3. The article of claim 2, wherein the density of the web ranges from 0.3 g/cc to 0.7 g/cc.

4. The article of claim 1, wherein the densified web has a wet pad integrity greater than the wet pad integrity of a non-bonded, densified web of cellulose fibers that has been densified to substantially the same degree.

5. The article of claim 1, wherein said article has an absorbent capacity that is at least about equivalent to a non-bonded, densified web of cellulose fibers.

6. The article of claim 1, wherein the article further comprises superabsorbent polymer distributed in said web in an amount effective to increase the absorbency of said web.

7. The article of claim 6, wherein the superabsorbent polymer is present in an amount up to about 70% by weight based on the weight of the fiber and polymer.

8. The article of claim 1, wherein said cellulose fibers are selected from the group consisting of non-cross-linked cellulose fibers, cross-linked cellulose fibers, cellulosic fibers containing a particle binder or a densification/softening agent, and mixtures thereof.

9. The article of claim 1, wherein the bonding agent comprises a thermoplastic or thermosetting material that is activatable by heating to a temperature above room temperature, when heated will contact the cellulose fibers, when deactivated will bond at least some of the cellulosic fibers together.

10. The article of claim 9, wherein the thermosetting material is selected from the group consisting of a phenolic resin, polyvinyl acetate, urea formaldehydes, melamine formaldehydes, and acrylics.

11. The article of claim 9, wherein the thermoplastic material is particles or fibers selected from the group consisting of thermoplastic polymers, cellulosic fibers coated with thermoplastic polymer, and multi-component fibers in which at least one of the components of the fiber comprises a thermoplastic polymer.

12. The article of claim 11, wherein the thermoplastic polymer is selected from the group consisting of polyester, polyethylene and polypropylene.

13. A fibrous article comprising:
    a densified web of cellulose fibers in which at least some of the cellulose fibers are bonded together by a bonding agent comprising a water insoluble, thermoplastic or thermosetting material, said web having been densified after the bonding agent has been deactivated and has bound the fibers together, said web having been densified while the bonding agent is deactivated, the densified web having an absorbent capacity for synthetic urine that is greater than the absorbent capacity for synthetic urine exhibited by a comparable web of cellulose fibers bound together by a bonding agent in which the comparable web has been densified to substantially the same degree as said densified comparable web by activating the bonding agent and densifying the web while the bonding agent is active.

14. The fibrous article of claim 13, wherein the densified web has a wet pad integrity greater than the wet pad integrity of a non-bonded web of cellulose fibers that have been densified to substantially the same degree.

15. The fibrous article of claim 13, wherein said cellulose fibers are selected from the group consisting of cross-linked cellulose fibers, non-cross-linked cellulose fibers, cellalosic fibers containing a particle binder or densification/softening agent, and mixtures thereof.

16. The fibrous article of claim 13, wherein the densified web has an absorbent capacity that is at least about equivalent to the absorbent capacity of a non-bonded, densified web of cellulose fibers.

17. The fibrous article of claim 13, wherein the densified web has a density equal to or greater than 0.1 g/cc.

18. The article of claim 17, wherein the densified web has a density ranging from about 0.1 to about 0.7 g/cc.

19. The article of claim 18, wherein said densified web has a density ranging from about 0.3 to about 0.7 g/cc.

20. The article of claim 13, wherein said densified web further comprises a superabsorbent polymer distributed through said densified web.

21. The article of claim 20, wherein the superabsorbent polymer is present in amounts ranging up to about 70% by weight based on the weight of the fiber and polymer.

22. The article of claim 13, wherein the bonding agent comprises a thermoplastic or thermosetting material that is activatable by heating to a temperature above room temperature, that when heated will contact the cellulose fibers, and when deactivated will bond at least some of the cellulose fibers together.

23. The article of claim 22, wherein the thermoplastic material is selected from the group consisting of particles or fibers comprising a thermoplastic polymer, cellulose fibers coated with a thermoplastic polymer, and multi-component fibers wherein at least one of the fiber components comprises a thermoplastic polymer.

24. The article of claim 23, wherein said thermoplastic polymer is selected from the group consisting of polyester, polypropylene, and polyethylene.

25. The article of claim 22, wherein the thermosetting material is selected from the group consisting of phenolic resin, polyvinyl acetate, urea formaldehydes, melamine formaldehydes, and acrylics.

26. An absorbent article for acquiring, distributing, or storing body fluids, the article comprising:
   an absorbent layer that includes a densified web of cellulose fibers in which at least some of the cellulose fibers are bonded together by a bonding agent comprising a water insoluble, thermoplastic or thermosetting material, said web having been densified after the bonding agent is deactivated and has bound the fibers together, said web having been densified while the bonding agent is deactivated, the densified web having a minimum density equal to or greater than 0.1 g/cc, based on the weight of the cellulose fiber and bonding agent.

27. The fibrous article of claim 26, wherein the densified web has a wet pad integrity greater than the wet pad integrity of a non-bonded web of cellulose fibers that has been densified to substantially the same degree.

28. The fibrous article of claim 26, wherein said cellulose fibers are selected from the group consisting of cross-linked cellulose fibers, non-cross-linked cellulose fibers, cellulosic fibers containing a particle binder or densification/softening agent, and mixtures thereof.

29. The fibrous article of claim 26, wherein the densified web has an absorbent capacity that is at least about equivalent to the absorbent capacity of a non-bonded, densified web of cellulose fibers.

30. The fibrous article of claim 26, wherein the densified web has a density equal to or greater than 0.1 g/cc.

31. The article of claim 30, wherein the densified web has a density ranging from about 0.1 to about 0.7 g/cc.

32. The article of claim 31, wherein said densified web has a density ranging from about 0.3 to about 0.7 g/cc.

33. The article of claim 26, wherein said densified web further comprises a super absorbent polymer distributed through said densified web.

34. The article of claim 33, wherein the superabsorbent polymer is present in amounts ranging up to about 70% by weight based on the weight of the fibers and the bonding agent.

35. The article of claim 26, wherein the bonding agent comprises a thermoplastic or thermosetting material that is activatable by heating to a temperature above room temperature, when heated will contact the cellulose fibers, and when deactivated will bond at least some of the cellulose fibers together.

36. The article of claim 35, wherein the thermoplastic material is selected from the group consisting of particles or fibers comprising a thermoplastic polymer, cellulose fibers coated with a thermoplastic polymer, and multi-component fibers wherein at least one of the fiber components comprises a thermoplastic polymer.

37. The article of claim 26, wherein said thermoplastic polymer is selected from the group consisting of polyester, polypropylene, and polyethylene.

38. The article of claim 35, wherein the thermosetting material is selected from the group consisting of phenolic resin, polyvinyl acetate, urea formaldehydes, melamine formaldehydes, and acrylics.

39. An absorbent article for acquiring, distributing, and storing bodily fluids, the article comprising:
   an upper acquisition/distribution layer for receiving body fluid from a source, the acquisition/distribution layer including a densified web of cellulose fibers in which at least some of the cellulose fibers are bonded together by a bonding agent comprising a water insoluble, thermoplastic or thermosetting material, said web having been densified after the bonding agent is deactivated and has bound the fibers together, said web having been densified while the bonding agent is deactivated, the densified web having a minimum density equal to or greater than 0.1 g/cc based on the average weight of the fibers and the bonding agent; and
   a storage layer for receiving body fluid from the acquisition/distribution layer, the storage layer including a densified web of cellulose fibers in which at least some of the cellulose fibers are bonded to each other by a bonding agent, said web having been densified after the bonding agent is deactivated and has bound the fibers together.

40. The article of claim 39, wherein the cellulose fibers in the upper acquisition/distribution layers are selected from the group consisting of non-cross-linked cellulose fibers, cross-linked cellulose fibers, and mixtures thereof.

41. The article of claim 39, wherein said acquisition/distribution layer further comprises a superabsorbent polymer for absorbing liquid components of the body fluids.

42. The article of claim 39, wherein said cellulose fibers in said storage layer are selected from the group consisting of non-cross-linked cellulose fibers, cross-linked cellulose fibers, cellulosic fibers containing a particle binder or densifying/softening agent, and mixtures thereof.

43. The article of claim 39, wherein the cellulose fibers in the storage layer comprise a densified web of fibers in which at least some of the cellulose fibers are bonded to each other by a bonding agent, the web having been densified after the bonding agent is deactivated and has bound the fibers together.

44. The article of claim 39, wherein the fibers in the storage layer further comprise a superabsorbent polymer for absorbing liquid components of the body fluids.

45. The absorbent article of claim 39, further comprising a lower distribution layer including a web of cellulose fibers, said cellulose fibers being selected from the group consisting of non-cross-linked fibers, cross-linked fibers, fibers containing a particle binder, and mixtures thereof.

46. The article of claim 45, wherein the lower distribution layer further comprises a superabsorbent polymer for absorbing liquid components of the body fluids.

47. The article of claim 39, wherein the bonding material comprises a thermoplastic or thermosetting material that is activatable by heating to a temperature above room temperature, when heated will contact the cellulose fibers, and when deactivated will bond at least some of the cellulose fibers together.

48. The article of claim 47, wherein the thermoplastic material is selected from the group consisting of particles or fibers comprising a thermoplastic polymer, cellulose fibers coated with a thermoplastic polymer, and multi-component fibers wherein at least one of the fiber components comprises a thermoplastic polymer.

49. The article of claim 48, wherein said thermoplastic material is selected from the group consisting of polyester, polypropylene, and polyethylene.

50. The article of claim 48, wherein said thermosetting material is selected from the group consisting of phenolic resin, urea formaldehydes, melamine formaldehydes, polyvinyl acetate, or acrylics.

51. A method for producing a densified web of cellulose fibers comprising:

forming a web of cellulose fibers containing a bonding agent comprising a water insoluble, thermoplastic or thermosetting material;

activating the bonding agent so that the bonding agent contacts at least some of the cellulose fibers;

thereafter deactivating the bonding agent to bind at least some of said cellulose fibers together; and thereafter densifying said web of cellulose fibers to a density of at least 0.1 g/cc, said web being densified while said bonding agent is deactivated.

52. The method of claim 51, wherein said web is densified to a density between 0.1 g/cc and 0.7 g/cc.

53. The method of claim 52, wherein said web is densified to a density ranging from 0.3 g/cc to about 0.7 g/cc.

54. The method of claim 51, wherein the densified web has a wet pad integrity greater than the wet pad integrity of a non-bonded, densified web of cellulose fibers that has been densified to substantially the same degree.

55. The method of claim 51, wherein the densified web formed by the method has an absorbent capacity that is at least about equivalent to a non-bonded, densified web of cellulose fibers.

56. The method of claim 51, further comprising incorporating a superabsorbent polymer into the web of cellulose fibers before activating the bonding agent.

57. The method of claim 56, wherein the superabsorbent polymer is present in an amount up to about 70% by weight based on the weight of the fiber and the bonding agent.

58. The method of claim 51, wherein the fibers are selected from the group consisting of cross-linked cellulose fibers, non-cross-linked cellulose fibers, cellulosic fibers containing a particle binder, and mixtures thereof.

59. The method of claim 51, wherein the bonding material comprises a thermoplastic or thermosetting material that is activatable by heating to a temperature above room temperature, when heated will contact at least a portion of the cellulose fibers and when deactivated will bond at least some of the cellulose fibers together.

60. The method of claim 59, wherein the thermoplastic material is selected from the group consisting of fibers or particles comprising a thermoplastic polymer, cellulose fibers coated with a thermoplastic polymer, and multi-component fibers wherein at least one of said components comprises a thermoplastic polymer.

61. The method of claim 59, wherein the thermoplastic material is selected from the group consisting of polyester, polyethylene, and polypropylene.

62. The method of claim 61, wherein the thermosetting material is selected from the group consisting of phenolic resin, urea formaldehydes, melamine formaldehydes, polyvinyl acetate, and acrylics.

63. The product produced by the method of claim 57, 58, 59, 60, 61 or 62.

* * * * *